(12) United States Patent
Greener et al.

(10) Patent No.: US 8,680,360 B2
(45) Date of Patent: Mar. 25, 2014

(54) LATTICE DRESSING

(75) Inventors: Bryan Greener, Yorkshire (GB); Allan Freedline, Miami Beach, FL (US)

(73) Assignee: Smith & Nephew Inc., Memphis, TN (US)

( * ) Notice: Subject to any disclaimer, the term of this patent is extended or adjusted under 35 U.S.C. 154(b) by 907 days.

(21) Appl. No.: 12/443,169

(22) PCT Filed: Sep. 26, 2007

(86) PCT No.: PCT/US2007/079529
§ 371 (c)(1),
(2), (4) Date: Nov. 17, 2009

(87) PCT Pub. No.: WO2008/039839
PCT Pub. Date: Apr. 3, 2008

(65) Prior Publication Data
US 2010/0100022 A1 Apr. 22, 2010

Related U.S. Application Data

(60) Provisional application No. 60/826,922, filed on Sep. 26, 2006.

(51) Int. Cl.
*A61F 13/00* (2006.01)
(52) U.S. Cl.
USPC .......... 602/47; 602/41; 602/42; 602/46
(58) Field of Classification Search
USPC .......... 602/41–59; 128/888, 889
See application file for complete search history.

(56) References Cited

U.S. PATENT DOCUMENTS

| 1,975,504 A | | 10/1934 | Formhals |
| 2,877,765 A | * | 3/1959 | Bunyan .................. 602/47 |
| 4,294,240 A | | 10/1981 | Thill |
| 4,418,691 A | | 12/1983 | Yannas et al. |
| 4,541,426 A | * | 9/1985 | Webster .................. 602/47 |
| 4,664,662 A | | 5/1987 | Webster |

(Continued)

FOREIGN PATENT DOCUMENTS

| EP | 1 614 789 | 1/2006 |
| GB | 821 959 | 10/1956 |

(Continued)

OTHER PUBLICATIONS

U.S. Appl. No. 10/652,100, filed Aug. 28, 2003, published as 2004/0073151, including its ongoing prosecution history, including without limitation Office Actions, Amendments, Remarks, and any other potentially relevent documents.

(Continued)

*Primary Examiner* — Kim M Lewis
(74) *Attorney, Agent, or Firm* — Knobbe, Martens, Olson & Bear, LLP

(57) ABSTRACT

A wound dressing, a method of manufacturing a wound dressing, and in particular to a material for use as and in a wound dressing. A wound dressing can comprise a material movable between an initial conformation and an expanded conformation resulting from applying an extensive force to the material, such that removal of the extensive force can cause a contraction of the material toward a center of a wound. In addition, the wound dressing can comprise a retaining mechanism removably coupled to the material and configured to retain the material in the expanded conformation.

30 Claims, 10 Drawing Sheets

(56) References Cited

U.S. PATENT DOCUMENTS

| | | | |
|---|---|---|---|
| 4,929,477 A | | 5/1990 | Will |
| 5,167,613 A | * | 12/1992 | Karami et al. ............... 602/42 |
| 5,267,952 A | | 12/1993 | Gardner |
| 5,397,316 A | * | 3/1995 | LaVon et al. ............... 604/369 |
| 5,415,715 A | | 5/1995 | Delage et al. |
| 5,489,304 A | | 2/1996 | Orgill et al. |
| 5,636,643 A | | 6/1997 | Argenta et al. |
| 5,645,081 A | | 7/1997 | Argenta et al. |
| 5,713,881 A | | 2/1998 | Rezai et al. |
| 5,716,411 A | | 2/1998 | Orgill et al. |
| 5,720,714 A | | 2/1998 | Penrose |
| 5,868,724 A | | 2/1999 | Diercket et al. |
| 5,981,822 A | * | 11/1999 | Addison ............... 602/41 |
| 6,167,613 B1 | | 1/2001 | Karmi |
| 6,203,654 B1 | * | 3/2001 | McFall et al. ............... 156/268 |
| 6,333,093 B1 | | 12/2001 | Burrell et al. |
| 6,713,659 B2 | | 3/2004 | Bodenschatz et al. |
| 6,752,794 B2 | | 6/2004 | Lockwood et al. |
| 6,942,628 B1 | | 9/2005 | Watson |
| 7,108,681 B2 | | 9/2006 | Gartstein et al. |
| 7,108,683 B2 | | 9/2006 | Zamierowski |
| 7,122,712 B2 | | 10/2006 | Lutri et al. |
| 7,438,705 B2 | | 10/2008 | Karpowicz et al. |
| 7,494,482 B2 | | 2/2009 | Orgill et al. |
| 7,676,400 B1 | * | 3/2010 | Dillon ............... 705/26.7 |
| 7,676,784 B2 | | 3/2010 | Allen et al. |
| 7,754,937 B2 | | 7/2010 | Boehringer et al. |
| 7,846,141 B2 | | 12/2010 | Weston |
| 7,896,856 B2 | | 3/2011 | Petrosenko et al. |
| 7,909,805 B2 | | 3/2011 | Weston |
| 7,982,087 B2 | | 7/2011 | Greener et al. |
| 8,062,272 B2 | | 11/2011 | Weston |
| 8,062,331 B2 | | 11/2011 | Zamierowski |
| 8,070,773 B2 | | 12/2011 | Zamierowski |
| 8,338,402 B2 | | 12/2012 | Fry et al. |
| 2001/0034499 A1 | * | 10/2001 | Sessions et al. ............... 602/46 |
| 2002/0193721 A1 | | 12/2002 | Vandruff |
| 2003/0050590 A1 | * | 3/2003 | Kirsch ............... 602/52 |
| 2003/0108587 A1 | | 6/2003 | Orgill et al. |
| 2004/0019337 A1 | | 1/2004 | Moberg-Alehammar et al. |
| 2004/0073151 A1 | | 4/2004 | Weston |
| 2005/0215932 A1 | | 9/2005 | Sigurjonsson et al. |
| 2005/0222544 A1 | | 10/2005 | Weston |
| 2005/0261642 A1 | | 11/2005 | Weston |
| 2006/0161123 A1 | | 7/2006 | Kudo et al. |
| 2007/0010775 A1 | | 1/2007 | Lutri |
| 2007/0032763 A1 | | 2/2007 | Vogel |
| 2007/0185426 A1 | | 8/2007 | Ambrosio et al. |
| 2007/0185463 A1 | | 8/2007 | Mulligan |
| 2008/0095979 A1 | | 4/2008 | Hatanaka et al. |
| 2008/0167593 A1 | | 7/2008 | Fleischmann |
| 2008/0300555 A1 | | 12/2008 | Olson et al. |
| 2009/0093550 A1 | | 4/2009 | Rolfes et al. |
| 2009/0105670 A1 | | 4/2009 | Bentley et al. |
| 2009/0105671 A1 | | 4/2009 | Daggar et al. |
| 2010/0010462 A1 | | 1/2010 | Kurata |
| 2010/0179463 A1 | | 7/2010 | Greener et al. |
| 2010/0196106 A1 | | 8/2010 | Allen |
| 2010/0249733 A9 | | 9/2010 | Blott et al. |
| 2010/0318046 A1 | | 12/2010 | Boehringer et al. |

FOREIGN PATENT DOCUMENTS

| | | | |
|---|---|---|---|
| GB | 821959 | * | 10/1959 |
| GB | 1 224 009 | A | 3/1971 |
| GB | 2 195 255 | A | 4/1988 |
| JP | H02-139624 | | 11/1990 |
| JP | H02-139625 | | 11/1990 |
| JP | H06-339495 | | 12/1994 |
| JP | H11-056900 | | 3/1999 |
| JP | 2004-000465 | | 1/2004 |
| WO | WO 90/10424 | | 9/1990 |
| WO | WO 92/10983 | | 7/1992 |
| WO | WO 95/14451 | | 6/1995 |
| WO | WO 96/01731 | | 1/1996 |
| WO | WO 97/11658 | | 4/1997 |
| WO | WO 02/092783 | | 11/2002 |
| WO | WO 03/072748 | | 9/2003 |
| WO | WO 2006/099137 | | 9/2006 |
| WO | WO 2008/039839 | | 4/2008 |
| WO | WO 2008/141228 | | 11/2008 |
| WO | WO 2009/021523 | | 2/2009 |
| WO | WO 2009/158131 | | 12/2009 |

OTHER PUBLICATIONS

U.S. Appl. No. 11/098,265, filed Apr. 4, 2005, published as 2005/0222544 A1, including its ongoing prosecution history, including without limitation Office Actions, Amendments, Remarks, and any other potentially relevent documents.

Application for Modification to HCPCS Level II Code Set in the 2005-2006 Coding Cycle. www.cms.hhs.gov/medicare/hcpcs/.

U.S. Appl. No. 12/300,636, filed Nov. 12, 2008, Fry et al.

U.S. Appl. No. 11/064,813, filed Feb. 24, 2005, published as 2005/0261642 A1, including its ongoing prosecution history, including without limitation Office Actions, Amendments, Remarks, and any other potentially relevant documents.

Alexander, J. Wesley et al., Clinical Evaluation of Epigard, A New Synthetic Substitute for Homograft and Heterograft Skin, The Journal of Trauma, vol. 13, No. 4, 1973, pp. 374-383.

Blumberg, Jack B. et al., The Effect of Specific Compression on Soft-Tissue Response to Formalinized PVA (Ivalon) Sponge: A Critical Evaluation, Annals Surg., Mar. 1960, 151(3), 409-418.

Boland et al., "Tailoring Tissue Engineering Scaffolds Using Electrostatic Processing Techniques: A Study of Poly(Glycolic Acid) Electrospinning" Journal of Macromolecular Science A. Pure and Applied Chemistry, A38(12), 1231-1243 (2001).

Boland E.D. et al. Utilizing acid pre-treatment and electrospinning to improve biocompatibility poly(glycolic acid) for tissue engineering. J. Biomed. Mater. Res. Part B: Appl Biomater 71B 144-152, 2004.

International Preliminary Report for International Application No. PCT/US2007/079529 date of mailing Apr. 8, 2008 in 6 pages.

International Search Report from PCT/GB2007/001713 mailed Dec. 11, 2007 in 5 pages.

International Search Report from PCT/US2007/079529 mailed Mar. 19, 2009 in 6 pages.

Ma, Peter X. Scaffolds for tissue fabrication. Materials Today, Review, May 2004.

Middleton, J., A. Tipton (Mar. 1998). "Synthetic biodegradable polymers as medical devices" (HTML). Medical Plastics and Biomaterials Magazine.

Stewart, Joanne, Ph.D., World Wide Wounds—Next generation of products for wound management—2002 (13 pages).

* cited by examiner

LATTICE DRESSING

CROSS-REFERENCE TO RELATED APPLICATIONS

This application is a U.S. National Phase of the PCT International Application No. PCT/US2007/079529, filed on 26 Sep. 2007, which claims priority to a U.S. Provisional Patent Application No. 60/826,922, filed on 26 Sep. 2006. The disclosure of both prior applications is incorporated by reference in their entirety and should be considered a part of this specification.

BACKGROUND OF THE INVENTION

1. Field of the Invention

The present invention relates to a wound dressing, a method of manufacturing a wound dressing, and in particular to a material for use as or in a wound dressing.

2. Description of the Related Art

Wound dressings are commonly manufactured from sheet materials. These materials include transparent films and adhesives and opaque foams and fibres. These materials generally retain their transparency or opacity upon fluid absorption, the exception being carboxymethylcellulose-based hydrofibre (which is initially opaque and becomes transparent when wet). Wound dressings which rely upon a foam element for exudate management are opaque and require removal and exchange for a new dressing during every wound inspection. This is a disadvantage of opaque dressings, for example, including a foam element. Foam-based dressings also have limited extensibility due to the mechanical properties inherent in a material of foam structure; this can cause problems when attempting to dress locations of high curvature. In spite of these performance disadvantages, the use of foam-based wound dressings or dressing elements dominates woundcare. This may be due to their excellent absorbency, low dry weight, cut-ability and mouldability. Limited extensibility is not restricted to foams; this is also a property of the films commonly applied in medical devices.

The single-axis lattice cutting of monolithic materials, including the sheet materials utilised in wound dressings has been disclosed in (GB821,959). However, once cut, these materials are not extended in any manner until post-application to the wound, and only then as a result of the flexing of the limb or other part of the body on which the dressing is worn. Whilst this type of dressing does enable some ease of movement for the patient, the material only permits minimal visibility of the wound. Additionally, the size of apertures and thus the permeability of the material, particularly important for the release of exudates from the wound, can not be controlled.

There is a need for a wound dressing which can be established in an extended conformation both prior to application and during application to a wound.

There is a need for a wound dressing which can be retained within a defined extended conformation both prior to application and during application to a wound.

There is a need for a wound dressing which allows visualisation of the wound immediately upon application of the dressing.

There is a need for a wound dressing which has a controlled aperture profile, which enables control of exudate egress.

There is a need for a wound dressing which has a controlled contractile profile for promoting wound closure.

SUMMARY OF THE INVENTION

The visibility through an opaque material can be increased by the creation of apertures through it. However, the creation of apertures, for example by hole-punching, has the disadvantages of resulting in the generation of waste and also the mechanical weakening of the material. By forming through slits in a material, these slits being capable of expanding to form apertures on extension of the material, we have been able to achieve both increased visibility of the wound and increased extensibility of the material, without significant material waste. In this manner, it is also possible to achieve extension of the slit to form a circular hole without mechanically weakening the material.

Therefore, according to an aspect of the invention there is provided a lattice comprising a material having at least one slit, the slit being capable of expansion into an aperture, the lattice having i) a first conformation, wherein the slit is substantially closed, and ii) a second conformation, wherein the lattice is stretched by the application of an extensive force expanding the slit to form an aperture having a first dimension.

Material having a slit or plurality of slits is referred to as a lattice, and prior to extension of the material, the lattice is referred to as being in a "first conformation" or "initial conformation" or "closed lattice conformation" wherein the slits are substantially closed. A substantially closed slit is a slit which has a conformation that allows no or substantially no visual inspection of the wound through the lattice with the naked eye.

Preferably, the material is a polyurethane foam or a silicone elastomer, for example.

The cutting of a largely two-dimensional or flat material and a three-dimensional material to form slits can be achieved by any means known in the art, for example laser cutting or blade pressing. The cutting method can be a batch process or continuous process. The cutting arrangements of two-dimensional material are preferably two-dimensional and along the x and y plane. The cutting arrangements of three-dimensional material are preferably three-dimensional and along the x, y and z planes.

The material may be cut so that the slits form a parallel, staggered, patterned or random arrangement.

Cuts are not restricted to any particular geometry; they may be straight-edged or curved. Straight-edged cuts include uni-directional arrangements, where all cuts are parallel, and multi-directional arrangements, where all cuts are non-parallel. Curved-cuts include arrangements radiating in an outwardly direction from a central point of the material and describing a circumference of a circle.

Generally speaking, the greater the number of cuts and thus excise of material, the more flexible and extensible will be the lattice formed from the material. However, the geometry of the cutting arrangement will also alter the mechanical properties of the material. Each different cutting geometry will provide a lattice having somewhat different mechanical properties and thus provide lattices of different flexibility and extensibility.

When cutting slits into the material to form the lattice, it is preferable that a minimum amount of material is removed. This avoids the detrimental effect on the structural integrity, and more particularly the mechanical strength of the lattice formed, which would otherwise happen where a larger amount of material was removed as in the case of the prior art where material is removed to form holes.

Preferably, the amount of material removed to form the lattice is therefore, for example, less than about 50% of the initial material volume, more preferably less than about 10% of the initial material volume, and ideally, less than about 1% of the initial material volume. Preferably, the excise of material to form the lattice gives rise to no or substantially no visual removal of material.

When the slits have been formed by cutting the material, the surface area of the resulting lattice can be extended, to about 25%-75% greater than the surface area of the original material. Extension of the lattice opens the slits forming a plurality of apertures/structural voids of a first dimension. The lattice in this extended form is referred to as an open lattice or having an "open lattice conformation", "second conformation" or "extended conformation".

The open lattice is established by an extensive force prior to or immediately prior to and during attachment to the site of application, for example, a wound site.

The lattice has a top or non-wound contacting surface and a bottom or wound contacting surface. The open lattice can be made from any suitable extendible material, for example, polyurethane foam.

The extensive force can be applied to the lattice in a unidirectional, bidirectional or isotropical manner and can be achieved by any means known to the skilled artisan, for example by drawing between rollers running at differential speeds. A process of extending the material in a controlled manner is considered particularly advantageous as this allows apertures/structural voids of predetermined dimensions and of particular interest to be formed.

Preferably, the lattice is extended to 25-75% of its maximum geometrical extension limit. The maximum geometrical extension limit is defined as the point at which the rate of change of the open volume or area of the apertures is zero or substantially zero. More preferably, the lattice is extended to maximise the open volume or area of the apertures, which may not necessarily be related to the maximum geometric extension.

Preferably, once the lattice has been extended into its second conformation, it can be retained in this conformation by the use of a retaining means. The retaining means may be adhered to a surface of the open lattice in any conventional manner. The retaining means can be a physical entity, such as a structural element, for example.

In an embodiment of the invention, the structural element can be a mechanically stiff backing layer, for example, the backing layer being stiff enough to maintain the extended open lattice conformation prior to and during application of the lattice to the wound site. The backing layer may comprise any suitable material, but is preferably plastic or paper.

Additionally the backing layer is easily releasable from the material.

The release of the backing layer maybe facilitated by a release tab or gripping portion associated with the backing layer.

The backing layer can be applied directly or indirectly to the open lattice, thus retaining and supporting it in the extended, or second or open lattice conformation prior to and during application. The backing layer has a sufficient mechanical stiffness to resist the inherent contractile force of the open lattice when the extensive force is removed, thereby retaining the lattice in the extended or open lattice conformation. Once the open lattice has been applied to the wound site the backing layer is removed. On removal of the backing layer, the contractile force is transferred to the wound site promoting closure of the wound. Removal of the backing layer also causes the surface area of the lattice and the volume of the voids established therein by the extensive force to shrink.

The extensive force applied to the lattice to form the open lattice is translated into a contractile force when the extensive force is removed. In embodiments of the invention more than about 10% of the extensive force is translated to a contractile force upon removal of the retaining means. In preferred embodiments of the invention more than about 50% of the extensive force is translated to a contractile force upon removal of the retaining means.

In this manner, a contractile force can be applied to the site of application. The use of such a lattice at a wound site, either directly or indirectly (for example, as part of a wound dressing) has the advantage of promoting wound closure, as a result of the contractile forces pulling the edges of the wound together.

By controlling the lattice and open lattice geometry (both the cut and the orientation of extension), it is possibly to control the geometry of the contractile force.

Upon removal of the retaining means, the open lattice preferably recovers more than 1% of the difference between its dimensions prior to extension and those same dimensions post-extension. More preferably, the open lattice recovers more than about 5% of the difference, and ideally recovers more than 10% of the difference.

In this embodiment of the invention, the greater the extension of the lattice the greater will be the contractile force on removal of the backing layer.

The invention is also concerned with the application of the open lattice both internally and externally of the body and on normal or injured tissue such that, following application of the open lattice, the extensive force can be released and transmitted to the attached tissue as a compressive force.

For the contraction of linear wounds, for example postoperative surgical incisions, lattices extensible along a single axis are preferred, as these lattices will impart contraction along a single axis, which when the lattice is appropriately position on the wound will be directed perpendicular to the line of the incision. For the contraction of two-dimensional wounds, for example chronic wounds such as pressure ulcers, lattices extensible along multiple axes are preferred.

Preferably, the lattice is extensible in a mechanically isotropic manner, enabling wound contraction to be directed towards the centre of the wound.

Alternative embodiments provide for the backing layer to be fixed to the non-wound contact surface of the open lattice. In this case the backing layer is a transparent material so that visual inspection of the wound is possible through the apertures of the lattice. It will be appreciated that in this embodiment, no contractile force is applied to the wound from the open lattice.

In another embodiment of the invention, the lattice can be of a material which allows it to also function as the retaining means. For example, the lattice can be made from so-called SMART materials (also referred to as shape-memory materials). The shape of SMART materials can be altered in a controlled fashion by external stimuli, such as stress, temperature, moisture, pH, electric or magnetic fields. In embodiments of the invention, the material is a SMART material. The lattice formed from the SMART material is extended into and retained in the second or open lattice conformation by the application of one or more external stimuli. Post-application of the open lattice to a wound site, further controlled exposure of the open lattice to an external stimulus would result in the open lattice fully or partially contracting to its original, "remembered" dimensions or first conformation. In a wound site, the open lattice could also be initiated or encouraged to contract by exposure to the moisture content of a wound exudate.

In another embodiment of the invention, the structural element can be a transparent film, for example a polyurethane film, fixedly or removably applied to the non-wound contact surface of the open lattice or to the non-wound contact surface and wound contact surface of the open lattice. The film is not as structurally rigid or stiff as the backing layer so that it can not hold the open lattice in a sufficiently extended form to provide a contractile force to promote closure of the wound if removed. Instead, the film keeps a more relaxed open conformation so that the slits remain apertures to allow visual inspection of the wound. The film of this embodiment also acts as a bacterial barrier which is particularly important when the lattice is administered to external wounds.

In further embodiments, both the film and backing layer may be used. The backing layer forms the external non-wound contacting surface and may be removable or fixed.

In yet a further embodiment, the lattice can be extended by hand. Gripping portions or tabs maybe provide at a periphery of the material to give the hand purchase, for example, aiding extension of the lattice by hand. The gripping tabs can be located to allow a more effective extension of the lattice and formation of apertures or structural voids from the slits. Once the lattice has been applied to the wound site the gripping portions are released. On release of the gripping portions, the contractile force of the open lattice is transferred to the wound site promoting closure of the wound. Release of the gripping portions also causes the surface area of the open lattice and the volume of the voids established therein, by the extensive force, to shrink. After the lattice has been secured to the wound site, the gripping portions can be removed from the lattice by cutting, for example. This will prevent the free ends of the gripping portions from snagging. Preferably, the lattice also has a polyeurethane film attached to both the wound and non-wound contact surfaces of the lattice. The polyurethane film will extend with the lattice to form an open lattice and will also act as a bacterial barrier.

In embodiments of the invention the lattice is a wound dressing. In alternative embodiments of the invention the lattice can form a part (for example a layer) of a wound dressing.

In an example of the lattice being incorporated into a wound dressing, a moisture permeable top-film can be applied to the non-wound contacting surface of the lattice (for example, by heat lamination), and the removable backing layer applied to the top-film. The top film can be a polyurethane film, for example. Optionally, a perforated layer of polyurethane film can be applied to the wound contact surface of the polyurethane foam lattice. The polyurethane film applied in this way will prevent the polyurethane foam sticking to the wound which may otherwise occur.

Therefore, according to a further aspect of the invention there is provided a wound dressing consisting of or comprising the lattice of the invention.

In an embodiment of this aspect of the invention the lattice material is a polyurethane foam and the retaining means is a backing sheet adhered temporarily to a non wound contacting surface of the lattice (for example, by a suitable adhesive or surface energy). The backing sheet is of a plastic material (for example, a polymeric film) or paper material (for example, reinforced paper or cardboard). The backing sheet is removed from the open lattice once the wound dressing has been applied to the wound by any suitable means known in the art, for example, by adhesive, sutures, staples or topical pressure.

Preferably, the material is sufficiently elastic to allow a return, unaided or unhindered, of the open lattice to the first conformation, wherein the slits are substantially dosed, after being stretched, deformed, compressed, or expanded. Materials conventionally utilised in wound dressings, such as foams (for example, polyurethane foam), silicone-based material (for example, a silicone elastomer), hydrofibre, films, non-woven and woven materials, demonstrate such elastic properties and are suitable materials.

Such elasticity results in the material exerting a spring-like contractile force following the removal of the extensive force, for example, by the removal of the retaining means. This contractile force results in the open lattice forming a "third conformation" or "contracted conformation", in which the apertures/structural voids are contracted to a smaller, second dimension.

In embodiments of the invention the material is a monolith.

According to a further aspect of the invention there is provided a wound dressing comprising a material having;
  i) an initial conformation,
  ii) an expanded conformation resulting from the application of an extensive force to the material, wherein the removal of the extensive force causes a contraction of the material, and
  iii) the wound dressing including means for retaining the material in the expanded conformation.

The material of this aspect of the invention is sufficiently expandable and contractible (partially or fully) from and to an initial conformation, without the requirement for the provision of slits. For example, the material can have elastic properties which closely resemble, for example, LYCRA® (Invista, US).

In an embodiment of this aspect of the invention, the material is provided with at least one slit and preferably with a plurality of slits.

According to a further aspect of the invention there is provided a method of promoting the closure of a wound, the method comprising the steps of;
  a) providing a material having a at least one slit to form a lattice, the slit being capable of expansion into an aperture, the lattice having:
  i) a first conformation, wherein the slit is substantially closed, and,
  ii) a second conformation, wherein the slit is expanded into an aperture having a first dimension,
  iii) retaining the lattice in the second conformation prior to application to a wound site,
  iv) applying the lattice in its second conformation to the wound site, and, optionally,
  c) allowing the lattice to retract from the second conformation towards the first conformation after application to the wound site.

In embodiments of the invention the open lattice can be applied directly to a wound. In alternative embodiments of the invention the open lattice can form a part (for example a layer) of a wound dressing which is applied to a wound.

The invention is particularly suited for application to topical and internal wounds, for example traumatic injuries, surgical incision wounds and open chronic wounds. Surgical wounds include those that are the result of plastics or maxillofacial operations, mastectomy or caesarean section.

The direction of the contractile force is influenced by the geometry of cut in the material to form the lattice, the geometry of extension of the lattice and the geometry of the attachment points between the lattice or wound dressing and the tissue.

The open lattice or wound dressing can be applied to the wound site using any suitable technique and attachment means known in the art, for example, adhesive, sutures, staples or topical pressure. Topical pressure can be provided by compression bandaging or atmospheric pressure acting upon a cavity of reduced pressure relative to the external atmosphere. Attachment can be achieved at specific locations on the open lattice or wound dressing or may cover the entire surface thereof. For topical applications, attachment is preferably achieved by an area exceeding 50% of the total area of the open lattice or wound dressing in contact with the site of application. More preferably, for topical applications, attachment is achieved by a pressure sensitive adhesive, for example an acrylate-based adhesive. Typically, the adhesive forms a layer on the wound contact surface of the open lattice or wound dressing.

According to a further aspect of the invention there is provided a method of manufacturing a wound dressing comprising the steps of,
(a) providing a first material,
(b) establishing the material in an extended conformation by applying an extensive force to at least part of the material, and
(c) retaining the material in the extended conformation by use of a retaining means.

Preferably, the method of manufacture includes the step of forming at least one slit and more preferably a plurality of slits in the material to form a lattice.

According to yet a further aspect of the invention there is provided a method of manufacturing a wound dressing comprising the steps of,
(a) providing a first material, and
(b) forming at least one slit in said first material to form a lattice.

Preferably, the method of manufacture includes the steps of,
(b) applying an extensive force to at least part of the lattice to establish the lattice in an extended or open conformation, and
(c) retaining the lattice in the extended or open conformation by use of a retaining means.

Examples of materials for use as the first material, include foams, such as polyurethane foam and silicone-based elastomers.

An example of a suitable material for use as the retaining means is a polymeric film, such as polyurethane film. Other suitable materials include polyester, polyethylene and polypropylene which can be perforated or extruded net.

BRIEF DESCRIPTION OF THE DRAWINGS

For a better understanding of the invention, a detailed description is made with reference to the accompanying drawings in which.

DETAILED DESCRIPTION OF THE PREFERRED EMBODIMENTS

Like reference numbers refer to corresponding parts throughout the drawings, description and examples.

EXAMPLE 1

To create the wound dressing of Example 1, a perforated sheet of polyurethane film was applied to the wound contact surface of a sheet of 4 mm depth polyurethane foam (Allevyn, Smith & Nephew Medical Limited).

The wound contact surface is that surface which is placed adjacent to or in direct contact with the wound. The non-wound contact surface is that surface which is remote from or opposite the wound contact surface.

Figure 1:
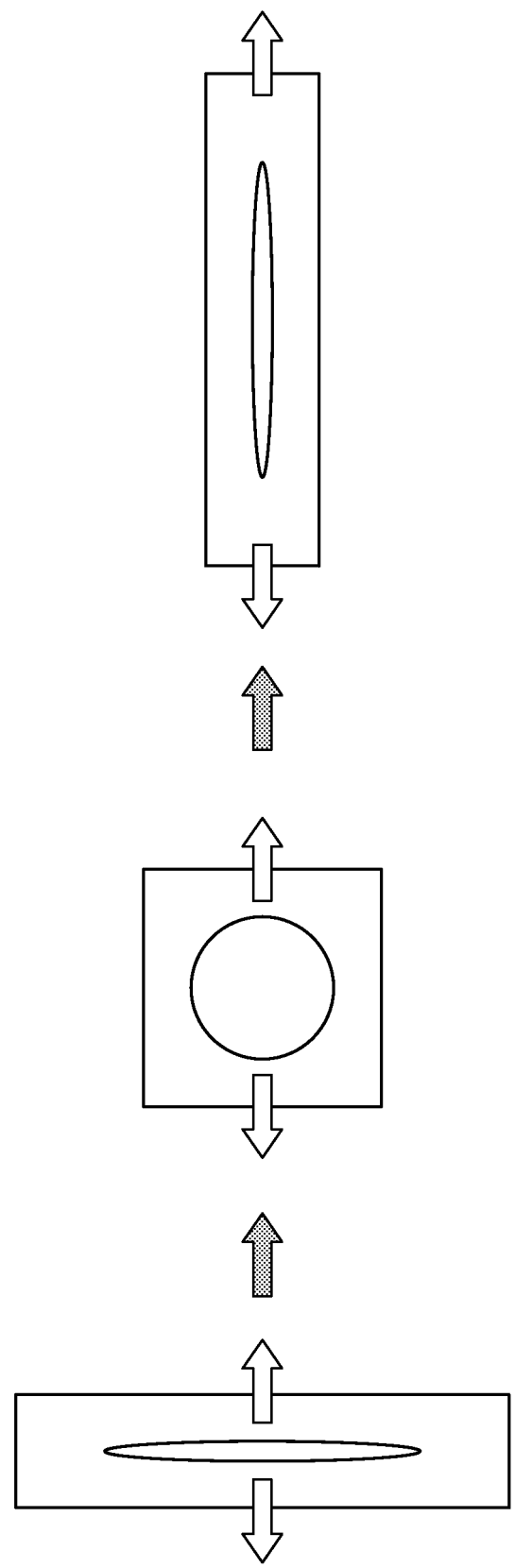
FIG. 1 demonstrates the extension of a slit, in three stages, under an extensive force, indicated by the arrows, and in a direction perpendicular to the longitudinal axis of the slit. The intermediate or second stage shows that the slit has been expanded to form a circle.
Figure 2:
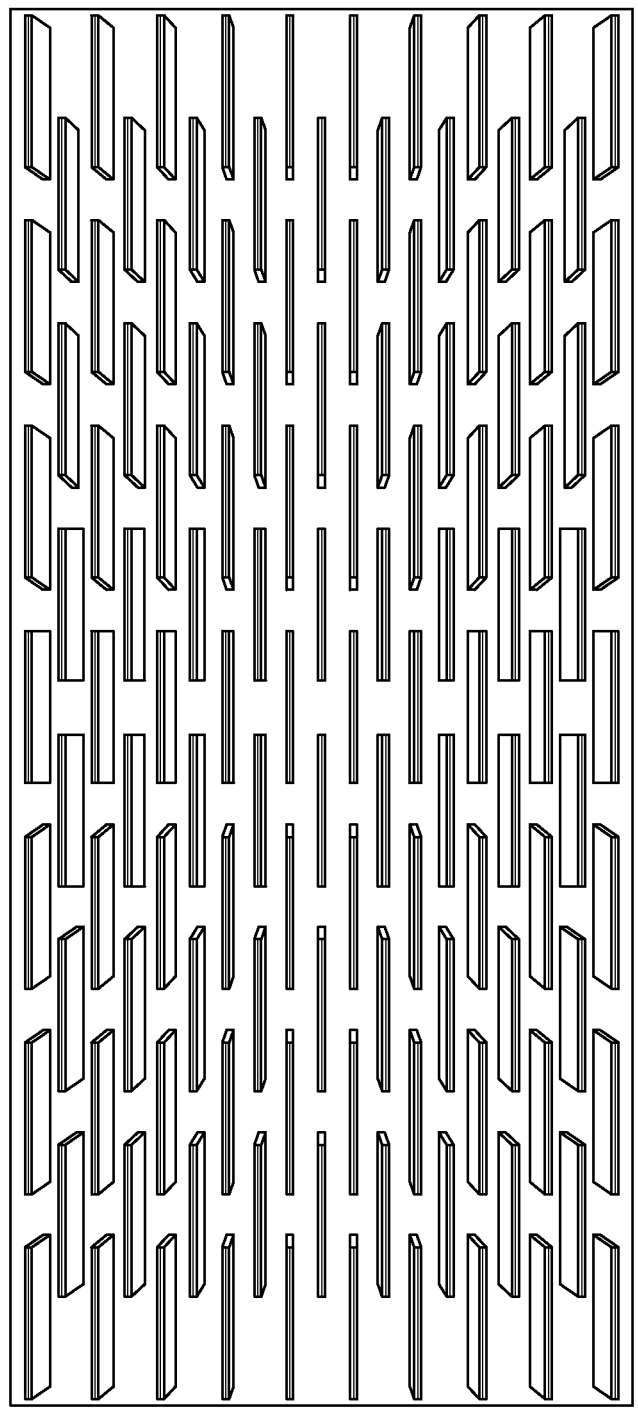
FIG. 2 is a plan view of a cutter for use in the manufacture of a first embodiment of lattice according to the invention.

A cutter of specification shown in FIG. 2 (Cutter blade with 15 mm length blades, linear spacing 5 mm, vertical spacing 5 mm) was used to cut slits in the sheet of polyurethane foam to form a lattice. The cutting action also formed slits in the polyurethane film.

Figure 3:
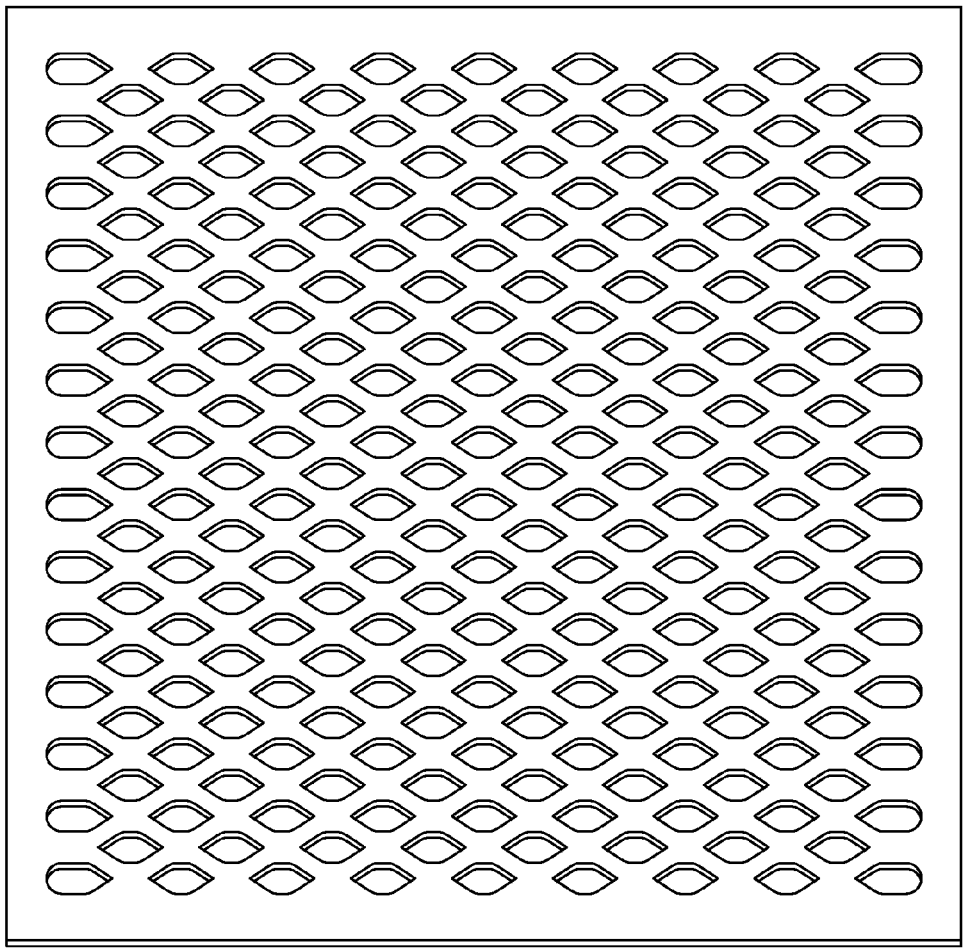
FIG. 3 is a plan view of the lattice formed using the cutter of FIG. 2, the lattice shown here in the open lattice or second conformation on application of a uni-directional extensive force applied perpendicular to the longitudinal axis of the slits.

Following cutting, an extensive force was applied to the lattice in a direction perpendicular to the longitudinal axis of the cuts or slits to produce an open lattice as shown in FIG. 3. A moisture permeable top-film was heat laminated to the non-wound contact layer or surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

EXAMPLE 2

To create the wound dressing of Example 2, a perforated sheet of adhesive polyurethane film was applied to the wound contact surface of a sheet of 4 mm depth polyurethane foam (Allevyn, Smith & Nephew Medical Limited). The adhesive surface of the film was covered by a siliconised release paper. A cutter of specification shown in FIG. 2 (Cutter blade with 15 mm length blades, linear spacing 5 mm, vertical spacing 5 mm) was used to cut slits in the sheet of polyurethane foam to form a lattice. The cutting action also formed slits in the polyurethane film and siliconised release paper.

The wound contact surface is that surface which is placed adjacent to or in direct contact with the wound. The non-wound contact surface is that surface which is remote from or opposite the wound contact surface.

Following cutting, the siliconised release paper was removed and an extensive force was applied to the lattice in a direction perpendicular to the longitudinal axis of the cuts or slits to produce the open lattice pattern as shown in FIG. 3. A new sheet of siliconised release paper was then attached to the wound contact surface of the perforated adhesive film. A moisture permeable top-film was heat laminated to the non-wound contact layer or surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

EXAMPLE 3

To demonstrate the effectiveness of the wound dressing of Example 2, the siliconised release paper was removed from the perforated adhesive film and placed, adhesive side down, upon intact skin. The polymeric film release sheet was then removed. A uni-directional contractile force was generated on the skin, upon removal of the polymeric film release sheet, and in a direction perpendicular to the axis of the cuts.

EXAMPLE 4

Figure 4:
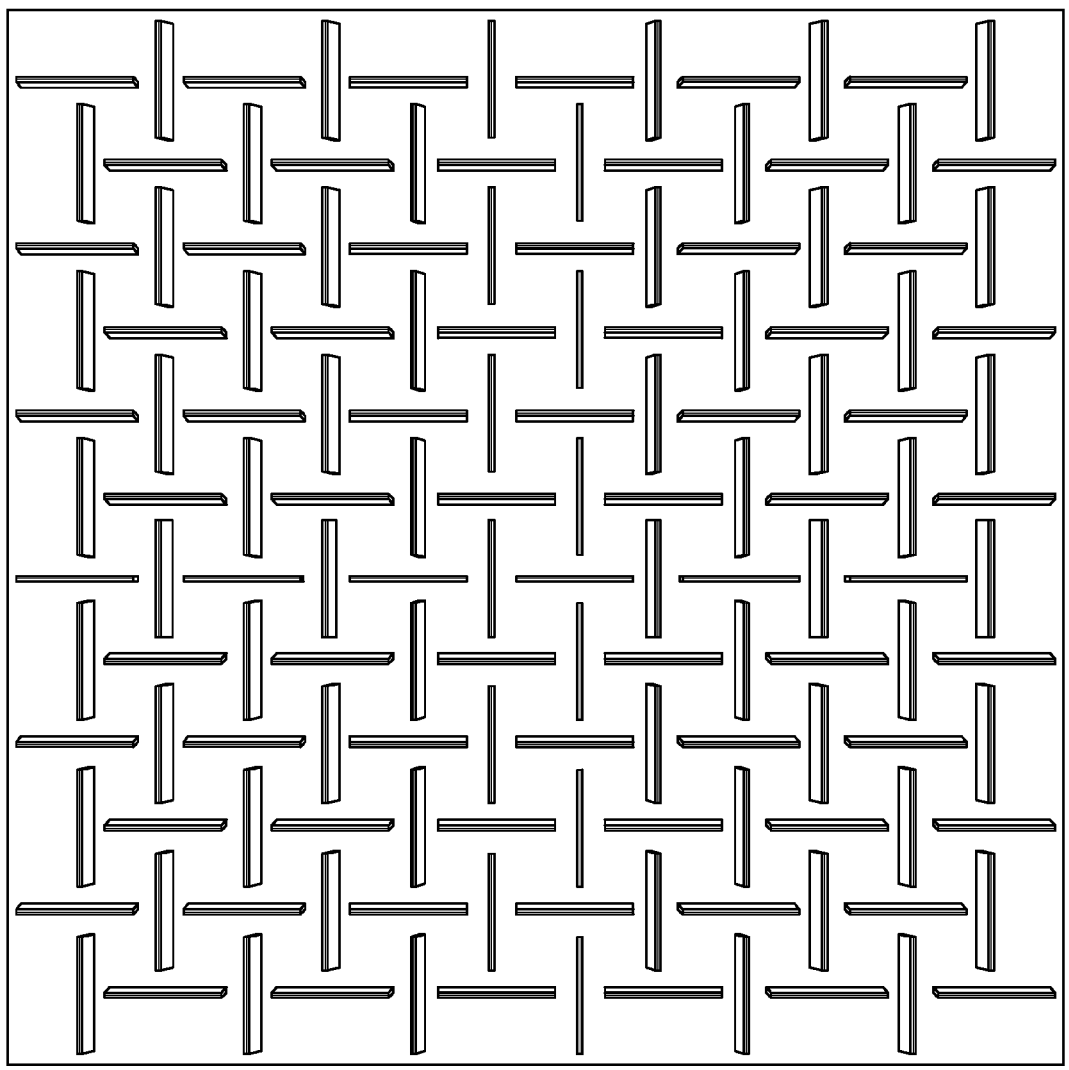
FIG. 4 is a plan view of a further cutter having a different cutting profile to the cutter of FIG. 2 for use in the manufacture of a second embodiment of lattice according to the invention.

To create the wound dressing of Example 4, a perforated sheet of polyurethane film was applied to the wound contact surface of a sheet of 4 mm depth polyurethane foam (Allevyn, Smith & Nephew Medical Limited). A cutter of specification shown in FIG. 4 (Cutter blade with 15 mm length blades, linear spacing 5 mm, vertical spacing 2.5 mm) was used to cut slits in the sheet of polyurethane foam to form a lattice. The cutting action also formed slits in the polyurethane film and siliconised release paper.

The wound contact surface is that surface which is placed adjacent to or in direct contact with the wound. The non-wound contact surface is that surface which is remote from or opposite the wound contact surface.

Figure 5:
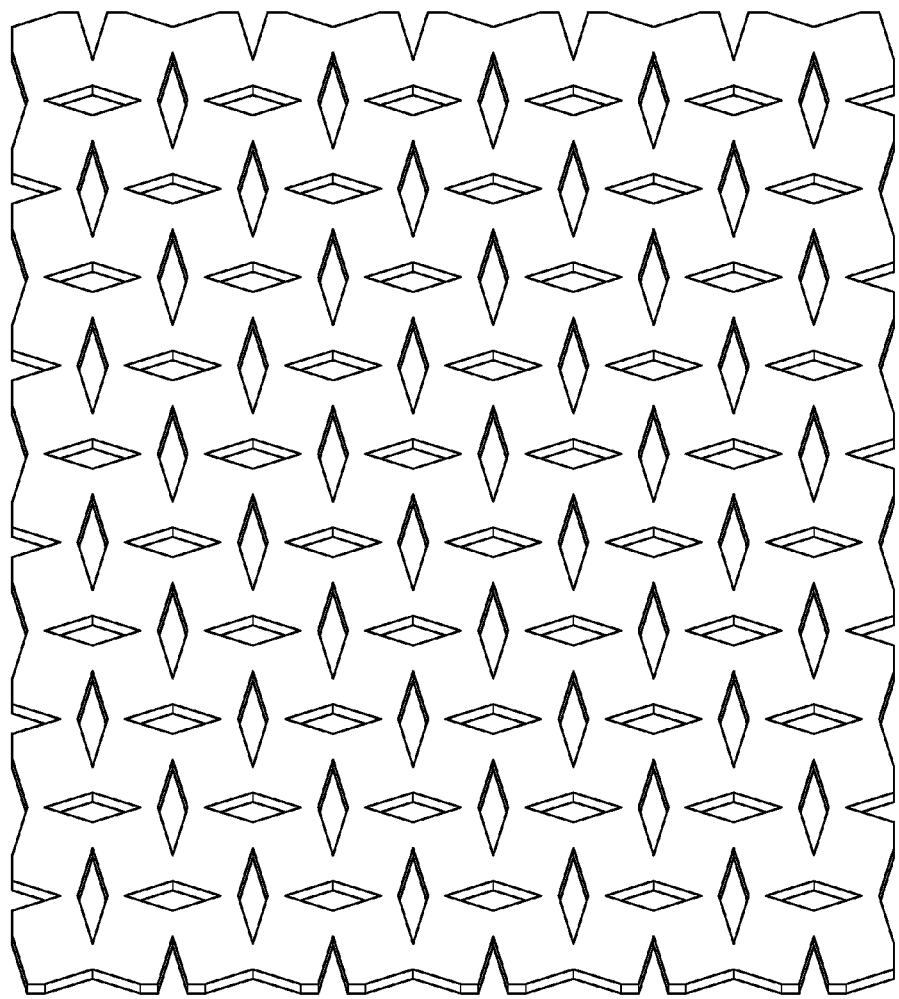
FIG. 5 is a plan view of the lattice formed using the cutter of FIG. 4, the lattice shown here in the open lattice or second conformation on application of a bi-directional extensive force applied perpendicular and parallel to the longitudinal axis of the slits.

Following cutting, the lattice was extended along two axes, x and y, as shown in FIG. 5. The extensive force was applied perpendicular and parallel to the longitudinal axis of the slits to produce an open lattice structure. A moisture permeable top-film was heat laminated to the non-wound contact surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

EXAMPLE 5

To create the wound dressing of Example 5, a perforated sheet of adhesive polyurethane film was applied to the wound contact surface of a sheet of 4 mm depth polyurethane foam (Allevyn, Smith & Nephew Medical Limited). The adhesive surface of the film was covered by a siliconised release paper. A cutter of specification shown in FIG. 4 (Cutter blade with 15 mm length blades, linear spacing 5 mm, vertical spacing 2.5 mm) was used to cut slits in the sheet of polyurethane foam to form a lattice. The cutting action also formed slits in the polyurethane film and siliconised release paper.

The wound contact surface is that surface which is placed adjacent to or in direct contact with the wound. The non-wound contact surface is that surface which is remote from or opposite the wound contact surface.

Following cutting, the siliconised release paper was removed and the lattice was extended along two axes, x and y, as shown in FIG. 5. The extensive force was applied perpendicular and parallel to the longitudinal axis of the slits to produce an open lattice structure. A new sheet of siliconised release paper was then attached to the wound contact surface of the perforated adhesive film. A moisture permeable top-film was heat laminated to the non-wound contact layer or surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

The lattice of the wound dressing of Example 5, having the polymeric film release sheet removed, is shown in FIG. 5.

EXAMPLE 6

To demonstrate the effectiveness of the wound dressing of Example 5, the siliconised release paper was removed from the perforated adhesive film and placed, adhesive side down, upon intact skin. The polymeric film release sheet was then removed. Upon removal of the polymeric film release sheet, a contractile force was generated on the skin acting towards the centre of the dressing.

EXAMPLE 7

Figure 6:
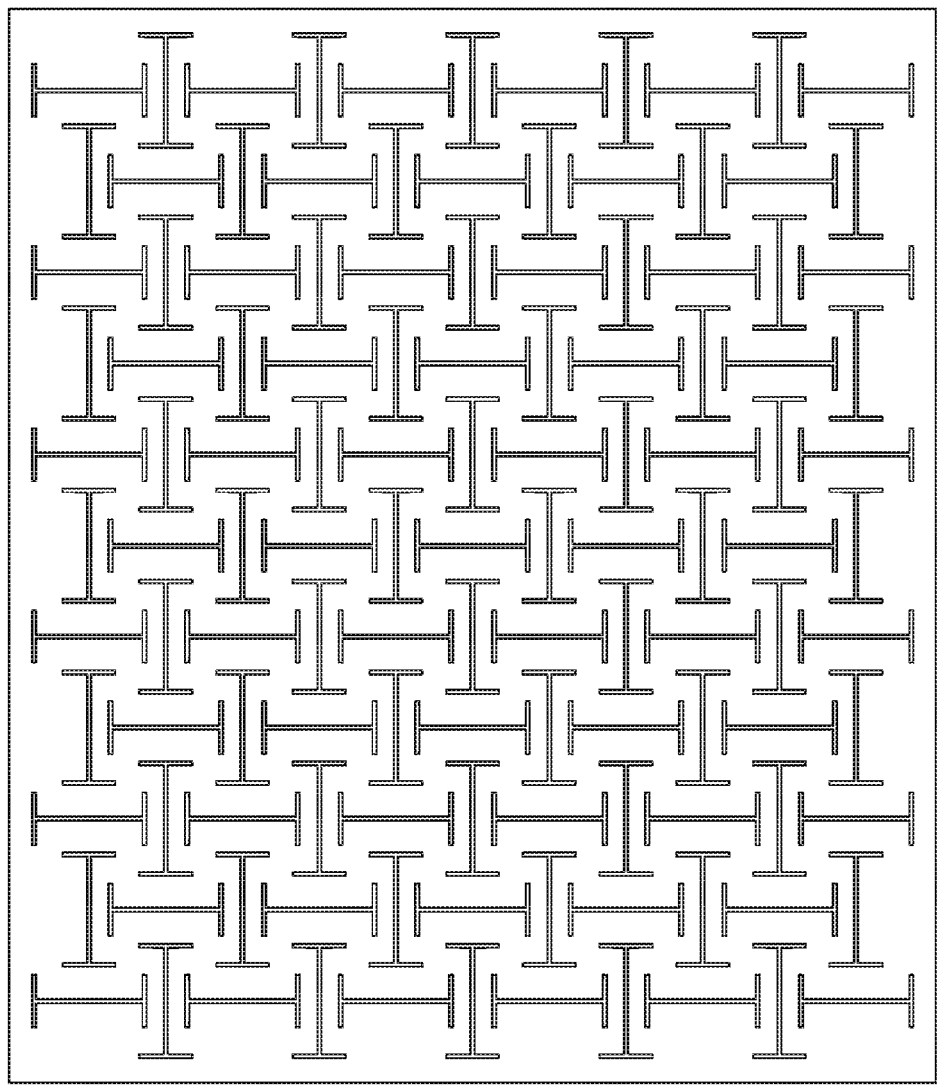
FIG. 6 is a schematic in plan view of yet a further a cutter, having an alternative cutting profile to the cutter of FIGS. 2 and 4, for use in the manufacture of a third embodiment of the lattice according to the invention.
Figure 7:
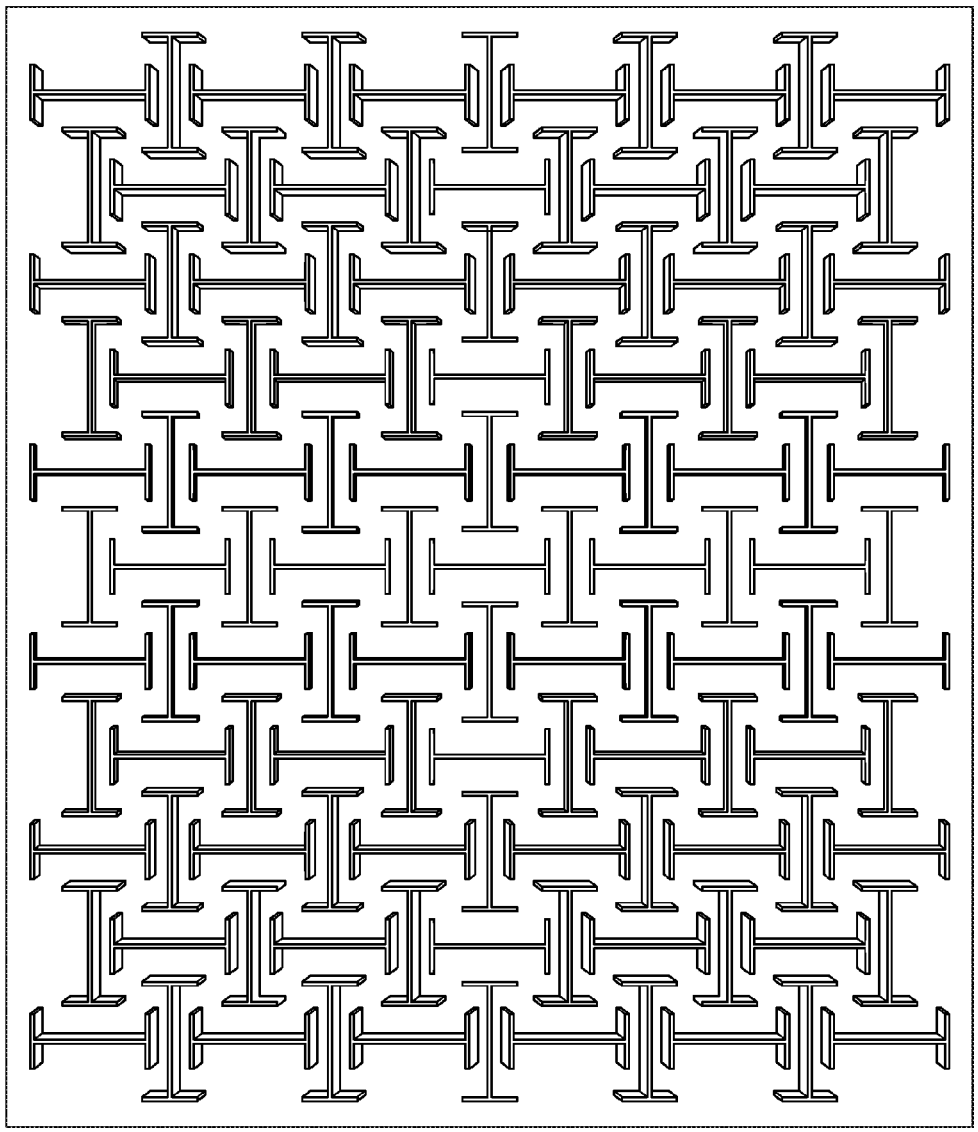
FIG. 7 is a plan view of the cutter manufactured according to the schematic of FIG. 6.

A similar process to that described for the wound dressing of Example 5 is employed to create the wound dressing of Example 7. However, in this case, a cutter of specification shown in FIGS. 6 and 7 was used to cut the slits. As can be seen from FIG. 6, the blades have three cutting edges. A long cutting edge of 15 mm in length bridging two shorter cutting edges of 7 mm in length. The two shorter cutting edges being parallel to each other and perpendicular to the longer cutting edge. Each blade has a spacing with an adjacent blade which describes a square area having a side length of 3.75 mm. This spacing is demonstrated by the shaded square portion in FIG. 6

Figure 8:
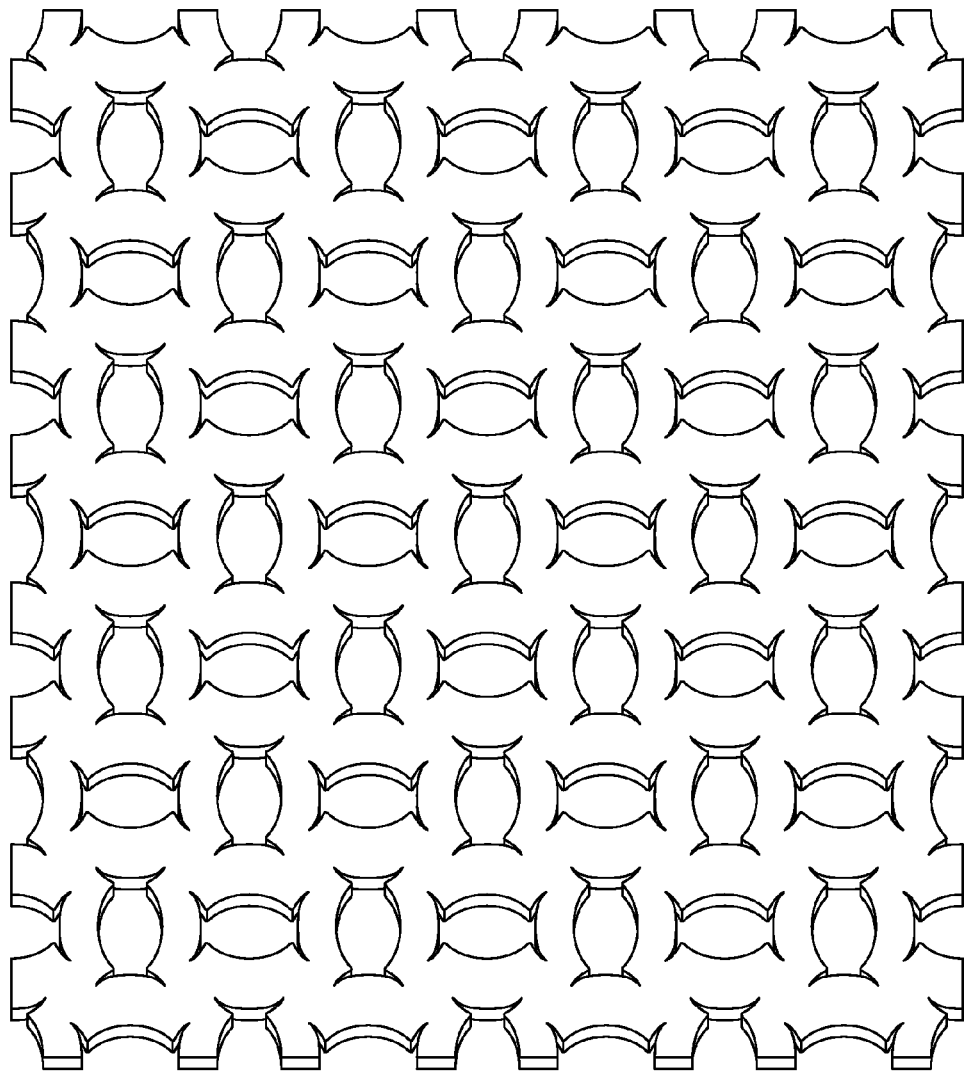
FIG. 8 is a plan view of the lattice formed using the cutter of FIG. 7, the lattice shown here in the open lattice or second conformation on application of a bi-directional extensive force applied perpendicular and parallel to the longitudinal axis of the slits.
Figure 9:
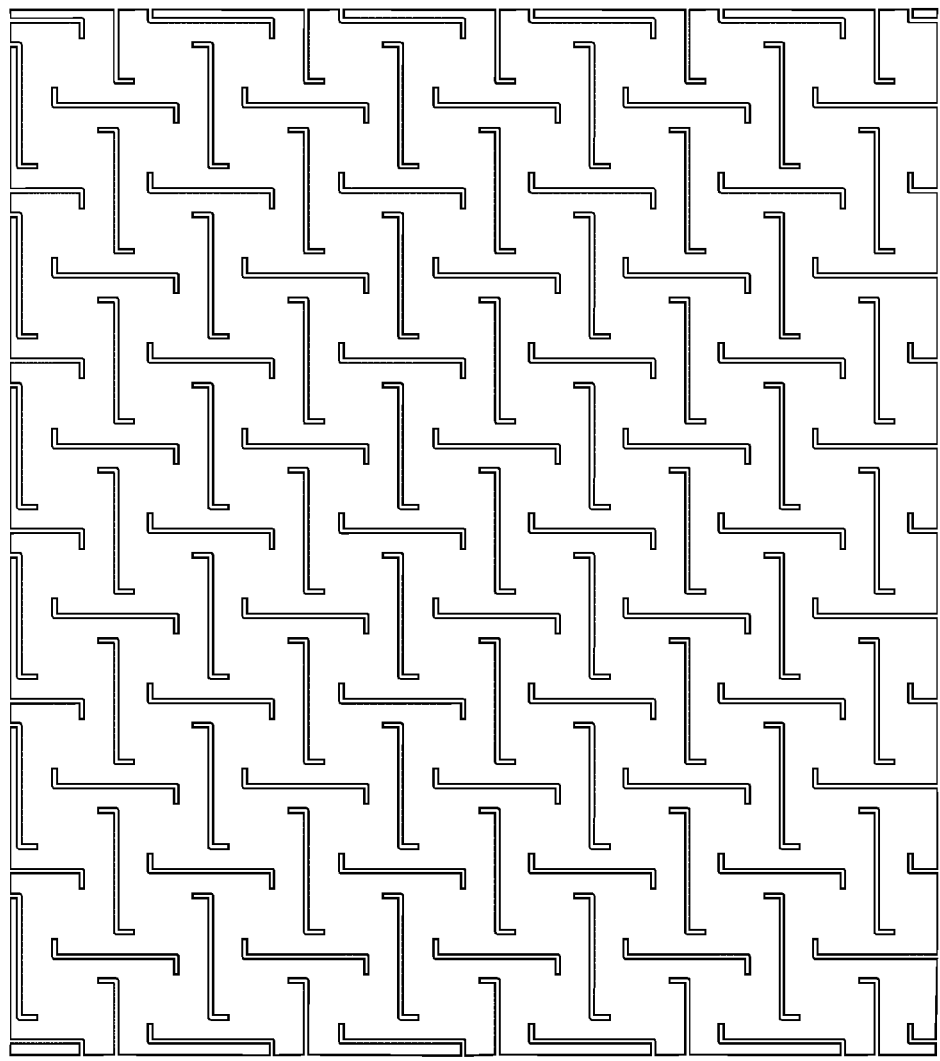
FIG. 9 is a plan view of the lattice formed using the cutter of FIG. 7, the lattice shown here in the first conformation where the slits are substantially closed. The lattice is opaque and the slits allow for no or substantially no visual inspection across the lattice.
Figure 10:
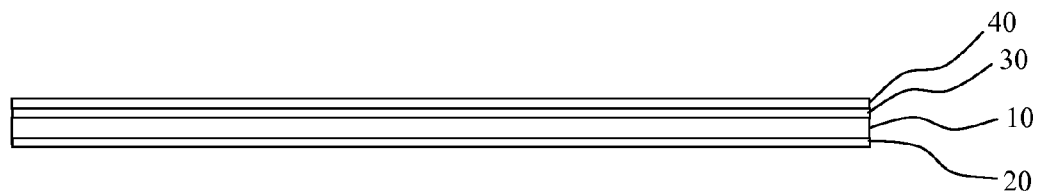
FIG. 10 is a schematic representation of a side view of an embodiment of a wound dressing having a foam layer 10, a film 20 coupled with a wound contact surface of the foam layer 10, and a layer 30 coupled with a non-wound contacting surface of the foam layer. A release sheet 40 can be applied to the film 30.

The lattice of the wound dressing of Example 7, having the polymeric film release sheet removed, it shown in FIG. 8.

What is claimed is:

1. A wound dressing comprising:
   an open lattice comprising:
      a porous wound dressing material;
      a film coupled to a wound contact surface of the porous wound dressing material;
      a plurality of open apertures in the porous wound dressing material; and
      a plurality of open apertures in the film coupled to the wound contact surface of the porous wound dressing material, the plurality of open apertures in the film being aligned with the open apertures formed in the porous wound dressing material; and
   a layer coupled with a non-wound contact surface of the porous wound dressing material of the open lattice and configured to support the open lattice in an open lattice conformation before the wound dressing is applied to a wound, the non-wound contact surface of the porous wound dressing material being opposite to the wound contact surface of the porous wound dressing material.

2. The wound dressing of claim 1, further comprising a backing layer releasably attached to at least one of the open lattice and the layer coupled with the non-wound contact surface of the porous wound dressing material of the open lattice.

3. The wound dressing of claim 2, wherein the layer coupled with the non-wound contact surface of the porous wound dressing material is not as structurally rigid as the backing layer.

4. The wound dressing of claim 2, wherein the backing layer is substantially rigid.

5. The wound dressing of claim 1 wherein, the wound dressing is configured to exert a contractile force on the wound during use.

6. The wound dressing of claim 1, wherein the porous wound dressing material is selected from the group consisting of: a monolith, a foam, a film, a non-woven material, and a woven material.

7. The wound dressing of claim 1, wherein at least one of the apertures is diamond shaped.

8. The wound dressing of claim 1, wherein at least one of the apertures is generally oval shaped.

9. The wound dressing of claim 1, wherein each of the plurality of open apertures is surrounded by a plurality of additional apertures having a different geometric orientation than the adjacent apertures.

10. A method of promoting the closure of a wound, comprising:
    placing the wound dressing of claim 1 onto a wound, the wound dressing being in an expanded conformation from application of an extensive force to the wound dressing; and
    releasing the wound dressing from the expanded conformation thereby causing the wound dressing to contract toward a center of the wound.

11. The method of claim 10, further comprising applying an isotropic extensive force to the wound dressing to move the wound dressing from a contracted conformation to the expanded conformation.

12. The method of claim 10, further comprising removing a backing layer from engagement with the wound dressing to release the wound dressing from the expanded conformation.

13. The method of claim 10, wherein each of the apertures is surrounded by a plurality of apertures having a different geometric orientation than the adjacent apertures.

14. The method of claim 10, wherein at least one of the apertures is diamond shaped.

15. The method of claim 10, wherein at least one of the apertures is oval shaped.

16. The wound dressing of claim 1, wherein the plurality of open apertures provide visual access to the wound bed in use.

17. The wound dressing of claim 1, wherein layer coupled with the non-wound contact surface of the porous wound dressing material of the open lattice comprises a film.

18. A wound dressing comprising:
    a material comprising:
        a foam layer;
        a film coupled with at least one surface of the foam layer; and
        a plurality of slits extending through the material so as to form a plurality of apertures that extend through the foam layer;
    an initial conformation; and
    an expanded conformation resulting from an application of an isotropic extensive force to the material wherein removal of the extensive force causes a contraction of the material directed toward a center of a wound; and
    a releasable backing layer removably coupled to the material;
    wherein:
        the material is an open lattice material comprising a plurality of slits extending through the foam layer aligned with a plurality of slits extending through the film forming a plurality of apertures that extend through the foam layer and the film;
        the plurality of apertures are in an open configuration in the expanded conformation such that the plurality of apertures are in an open configuration; and
        the backing layer is releasably applied to the material when the material is in its expanded conformation so that the wound dressing can be applied to a wound with the plurality of apertures being in the open configuration.

19. The wound dressing of claim 18, wherein, in use, the releasable backing layer supports the material in the expanded conformation.

20. The wound dressing of claim 18, wherein the releasable backing layer is a polymeric film.

21. The wound dressing of claim 18, wherein the plurality of slits extending through the material form a plurality of apertures that continuously extend through the foam layer and the film.

22. A method of manufacturing a wound dressing comprising:
    forming a plurality of slits in a material to form the wound dressing of claim 1 having an aperture pattern, wherein:
        the wound dressing comprises a first aperture that is surrounded by a plurality of apertures having a different geometric orientation than the first aperture;
        the material is movable from a contracted conformation to an expanded conformation; and
        the aperture pattern is configured to exert an isotropic contraction force on the material directed toward a center of a wound upon which the wound dressing has been placed.

23. The method of claim 22, wherein the plurality of apertures is formed by cutting the material with a blade or laser.

24. The method of claim 23, wherein the material is cut along two planes.

25. The method of claim 23, wherein the material is cut along three planes.

26. The method of claim 23, wherein the cutting of the material results in the removal of less than 10% of the material.

27. The method of claim 23, wherein the cutting of the material results in the removal of less than 1% of the material.

28. A wound dressing comprising:
    a material comprising:
        a plurality of apertures, wherein each aperture is surrounded by a plurality of apertures having a different geometric orientation than the apertures surrounded by the plurality of apertures;
        an initial conformation;
        an expanded conformation resulting from an application of an external stimulus to the material, wherein removal of the external stimulus causes a contraction of the material to the initial conformation; and
    a film coupled with the material when the material is in the expanded conformation;

wherein the film is configured to support the material such that the plurality of apertures are held in an open configuration.

29. The wound dressing of claim 28, wherein:
the external stimulus is an isotropic extensive force applied to the material; and
the removal of the external stimulus causes contraction of the material toward a center of a wound.

30. The wound dressing of claim 28, wherein the external stimulus is moisture content of a wound exudate.

* * * * *

UNITED STATES PATENT AND TRADEMARK OFFICE
CERTIFICATE OF CORRECTION

PATENT NO. : 8,680,360 B2  
APPLICATION NO. : 12/443169  
DATED : March 25, 2014  
INVENTOR(S) : Greener et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1143 days.

Signed and Sealed this

Twenty-ninth Day of September, 2015

Michelle K. Lee  
*Director of the United States Patent and Trademark Office*